Figure 1:
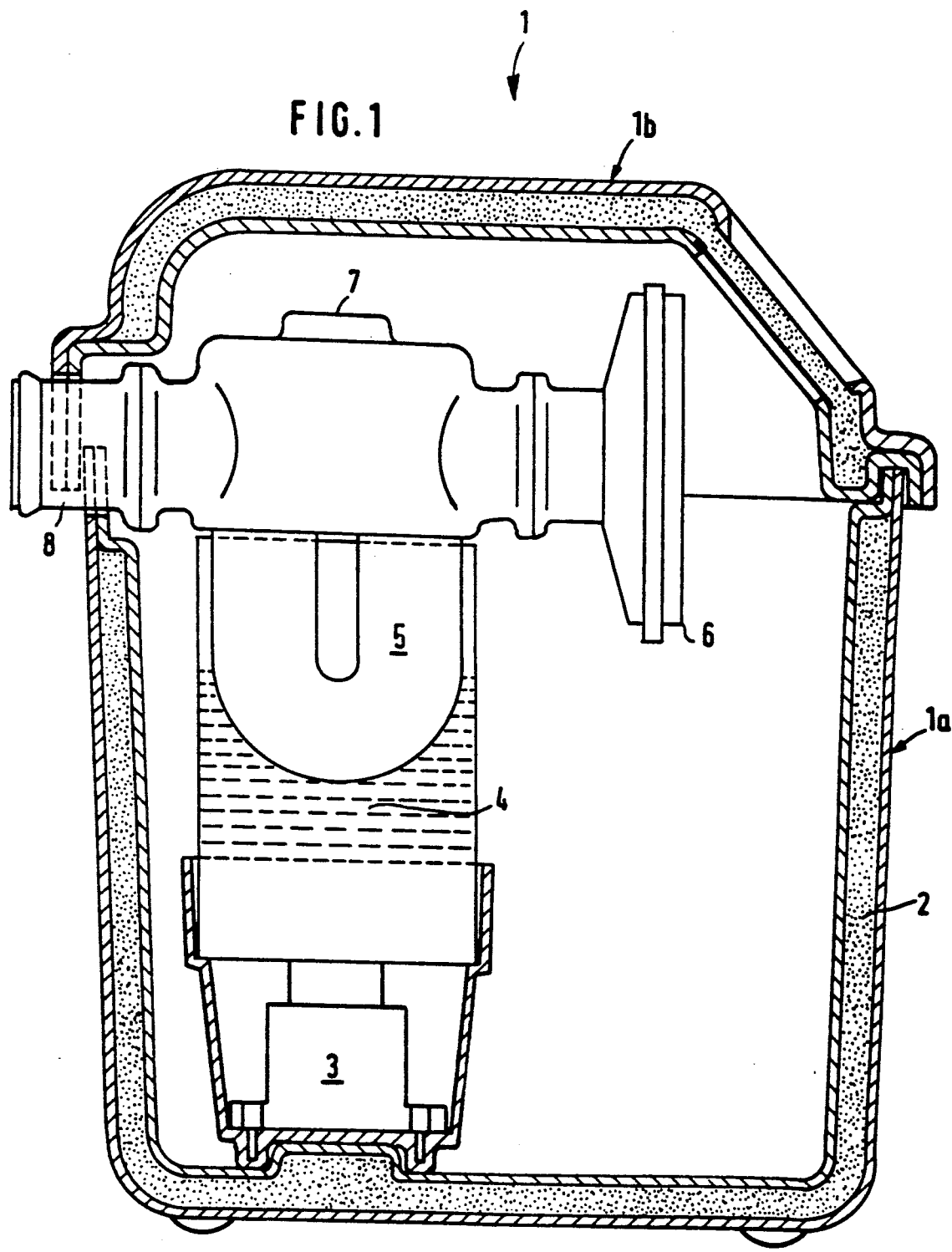

United States Patent

Waser

[11] Patent Number: 5,139,016
[45] Date of Patent: Aug. 18, 1992

[54] PROCESS AND DEVICE FOR AEROSOL GENERATION FOR PULMONARY VENTILATION SCINTIGRAPHY

[75] Inventor: John Waser, Basel, Switzerland
[73] Assignee: Sorin Biomedica S.p.A., Saluggia, Italy
[21] Appl. No.: 458,991
[22] Filed: Dec. 29, 1989

Related U.S. Application Data

[63] Continuation-in-part of Ser. No. 228,997, Aug. 5, 1988, abandoned.

[30] Foreign Application Priority Data

Aug. 7, 1987 [CH] Switzerland ............. 3042/87

[51] Int. Cl.$^5$ .................. A61M 11/00
[52] U.S. Cl. .................. 128/200.16; 128/200.14
[58] Field of Search ............. 128/200.14, 200.16

[56] References Cited

U.S. PATENT DOCUMENTS

| | | | |
|---|---|---|---|
| 3,561,444 | 2/1971 | Boucher | 128/200.16 |
| 3,690,317 | 9/1972 | Millman | 128/200.16 |
| 3,746,000 | 7/1973 | Edwards | 128/200.16 |
| 3,774,602 | 11/1973 | Edwards | 128/200.16 |
| 3,812,854 | 5/1974 | Michaels et al. | 128/200.16 |
| 4,094,317 | 6/1978 | Wasnich | 128/200.16 |
| 4,268,460 | 5/1981 | Boiarski et al. | 128/200.16 |
| 4,741,331 | 5/1988 | Wunderlich | 128/200.14 |

Primary Examiner—Edgar S. Burr
Assistant Examiner—Aaron J. Lewis
Attorney, Agent, or Firm—Wenderoth, Lind & Ponack

[57] ABSTRACT

A disposable shielded device for producing aerosol having particles less than 2 microns in size from an aqueous colloidal suspension obtained from human serum albumen and labelled with $^{99m}$Technetium for use in scintigraphic imaging of pulmonary function. The device includes a nebulizing chamber having a membrane of 0.1 mm to about 0.01 mm in thickness and 40 mm to about 50 mm in diameter which nebulizes the labelled substance in response to ultrasound waves transmitted thereto.

8 Claims, 3 Drawing Sheets

PROCESS AND DEVICE FOR AEROSOL GENERATION FOR PULMONARY VENTILATION SCINTIGRAPHY

CROSS-REFERENCE TO RELATED APPLICATION

This application is a continuation-in-part of co-pending application Ser. No. 07/228,997 filed Aug. 5, 1988, now abandoned.

FIELD OF THE INVENTION

The present invention relates to a method for producing radio-labelled aerosols for use in the scintigraphic measurement of pulmonary ventilation and to an apparatus for producing such aerosols.

BACKGROUND OF THE INVENTION

Ventilation scintigraphy and inhalation scintigraphy are two known scintigraphic methods for measuring regional pulmonary ventilation. They are particularly useful in diagnosing medical conditions such as pulmonary embolism, bronchial carcinoma and chronic obstructive pulmonary disease. In both methods, the patient inhales radioactive gases, for example krypton or xenon, or particles which have been labelled with radioactive particles. The radioactivity in the lungs is then measured with a gamma camera, a scanner or some other similarly suitable detector and is subsequently evaluated.

The use of krypton or xenon gases, as disclosed in U.S. Pat. Nos. 3,881,463 to LeMon and 4,706,683 to Chilton et al., suffers from numerous disadvantages. For instance, the relatively short half-lives (about 15-30 seconds) of xenon and krypton require that the scan be performed very shortly after administration of the gas. Therefore, it is more likely that additional administrations will be necessary if the scan needs to be repeated. Furthermore, methods of ventilation scintigraphy utilizing these radioactive gases suffer from the drawback that xenon and krypton are very scarce and hence expensive, as well as being subject to other difficulties in their administration.

The generation of an aerosol having monodisperse particles, i.e. particles of a relatively uniform size, less than 2 microns in diameter has proven to be critical to the diagnostic value of ventilation scintigraphy according to George V. Taplin in his article "Lung perfusion-inhalation, scintigraphy in obstructive airway disease and pulmonary embolism" *Radiologic Clinics of North America*, Vol. XVI., No. 3, December 1978. Taplin explains that if a large proportion of the particles in a scintigraphy aerosol exceed 2 microns in diameter, then undesireable tracheal and bronchial hyperdeposition of the aerosol occurs, i.e., the radioactive particles do not penetrate the lungs sufficiently to give diagnostically useful images.

The two major types of methods for generating respiratory aerosols which are known in the prior art are compressed air nebulization and ultrasound nebulization. The known methods have proven to be inconsistent for producing scintigraphy aerosols which meet the criterion established in the Taplin article.

Aerosol generation devices based on compressed air nebulization methods are disclosed in U.S. Pat. Nos. 4,510,929 to Gordoni et al., 4,660,547 to Kremer et al., 4,741,331 to Wunderlich, 4,782,828 to Burnett et al. and 4,803,977 to Kremer. As a representative example, U.S. Pat. No 4,660,547 to Kremer, et al. discloses aerosol generation by means of a compressed air system which utilizes to rather cumbersome radiation safety controls and procedures. The alternative source of compressed air, i.e. the hospital's own compressed air system, suffers from the disadvantage that the pressure generated thereby is usually subject to wide variation and therefore cannot provide the monodispersity required for accurate ventilation scintigraphy. Furthermore, compressed air aerosol generating systems may suffer from the disadvantage that the aerosol is forced into the patient's trachea, rather than being inhaled, possibly increasing the hyperdeposition of the radioactive aerosol in the airway instead of the bronchioles and the lungs.

A second method for generating an aerosol is by means of ultrasound. The devices disclosed in U.S. Pat. No. 3,774,602 to Edwards and German Patent No. 1,813,776 to Bahr et al. use an ultrasonic generator for producing aerosols adapted specifically for use in inhalation therapy and, therefore, the droplets produced thereby can be up to 6 microns in size (i.e. a size which greatly exceeds the recommended size of 2 microns). U.S. Pat. No. 4,094,317 to Wasnich discloses an example of an ultrasound nebulization system intended for use in inhalation scintigraphy in which the radioactively-labelled substance is contained at the bottom of a nebulizing chamber. The nebulizing chamber is surrounded by an ultrasound-conducting medium received in a container, at the bottom of which rests an ultrasonic generator. The droplets of the aerosol generated by this system vary greatly in size and the nebulizing chamber is actually designed to produce droplets in a size range of about 0.5 microns to about 3.5 microns. An impaction sphere is provided to trap droplets whose diameter exceeds 3.5 microns, causing the droplets to condense and recollect at the bottom of the nebulizing chamber where they are reatomized. A disadvantage of this system is that many of the particles allowed to pass are still larger than 2 microns which, as previously noted, is the maximum size preferred for effective diagnosis.

An additional problem is encountered when using ultrasound nebulization systems. Specifically, it has been found that the ultrasonic energy tends to disrupt the bond between most carrier media and the label. This disruption results in an undesirable amount of free radioactive labels leading to false clinical results. Therefore, choosing a suitable carrier medium and label itself has proven to be a significant problem.

There are no other methods known in the prior art which will ensure the production of an aerosol in which a high proportion of the aerosol particles are 2 microns or less in size. The possibility of using filters designed to prevent the passage and inhalation of particles larger than 2 microns is impractical because of the considerable air-flow restrictions imposed by such filters. An air-resistance which is too high must be avoided because most patients with severe lung damage, for whom scintigraphic investigations are of particular importance, are unable to inhale the aerosol to an extent adequate for accurate diagnoses.

The prior art systems also encounter difficulties in delivering a sufficient amount of the radioactive label to the lungs without exposing operators to large doses of radiation. For instance, the method disclosed in the Wasnich patent requires the injection of 20–30 mCi of $^{99m}$technetiumphytate ($^{99m}$Tc-phytate) in a 0.5 ml dose into the nebulizer for use in inhalation scintigraphy. Of that dose, only about 0.5 mCi actually penetrates the lungs. This relatively low yield makes tapping a fresh source of $^{99m}$Tc-phytate necessary, thereby increasing the cost of the test as well as the risk of radiation exposure to the technician. The situation is further aggravated by the fact that many of the labelled particles are too large to be useful.

The methods disclosed in at least some of the prior art patents discussed above have a further disadvantage in that they require extreme care in handling the radioactive substances or they do not provide adequate protection against radiation exposure for the technician. For example, the device disclosed in the Wasnich patent is unshielded. Combined with the relatively high doses of $^{99m}$Tc-phytate required, the lack of adequate shielding together with the need for multiple doses make it likely that a technician could only administer the scintigraphy a small number of times before exceeding recommended radiation exposure levels.

SUMMARY OF THE INVENTION

The present invention relates to a disposable apparatus for producing radio-labelled aerosol for use in the scintigraphic measurement of pulmonary ventilation and to the method for using said apparatus. The apparatus, which is described in greater detail below, is designed to be used once to eliminate the need for cleaning same. Additionally, the unitary construction described as the preferred embodiment reduces the possibility of exposure to radiation from the radioactive substances which are delivered to the patient in the form of a fine aerosol.

The present invention utilizes ultrasound waves to nebulize the labelled substance into particles having a size no greater than 2 microns. The apparatus is comprised of a shielded container having mounted at its bottom an ultrasonic generator. A nebulizing chamber having a very thin lower portion (between 0.01 mm to about 0.1 mm, and preferrably between 0.02 mm to about 0.03 mm) is suspended in the container which is partially filled with an ultrasound conducting medium such as water. The container is sufficiently filled with the conducting medium to submerge the thin portion or diaphragm of the nebulizing chamber suspended therein. The diaphragm is designed to provide maximum atomization of the labelled substance.

The nebulizing chamber is connected at one side of its upper portion to a filter which allows the patient to inhale and exhale numerous times. The filter prevents any of the labelled substance from escaping into the environment. At the side of the nebulizing chamber's upper portion opposite the filter, there is attached a breathing tube which exits the sealed, lined container. A chamber containing a series of baffles is incorporated within the breathing tube adjacent to the nebulizing chamber. At the top of the nebulizing chamber there is located an injection port and a sliding bar which slides over the injection port and irreversibly locks in place after the labelled substance is injected into the nebulizing chamber.

The labelled substance which is preferrably used in conjunction with the apparatus of the present invention is a physiologically degradeable colloidal material. The colloid is derived from human serum albumen (HSA) in accordance with a process described in U.S. Pat. No. 4,410,507, the specification of which is incorporated herein by reference. The colloid is presently marketed by Solco Basle Ltd., a Swiss corporation, under the trademark SOLCO VENTICOLL and has an irregular surface structure which promotes a strong bond between the colloid and a radioactive label comprised of technetium-99m ($^{99m}$Tc). It has been noted that the bond between SOLCO VENTICOLL and $^{99m}$Tc is stronger and has a lesser tendency to become detached than that of conventional radioactively labelled substances. Investigations have suggested that the irregular surface of SOLCO VENTICOLL is responsible for this phenomena. An additional advantage of using SOLCO VENTICOLL is that it can be reliably produced in sizes less than 2 microns. Moreover, $^{99m}$Tc has a half-life of about six hours which allows numerous scans to be performed in a less hasty manner than is possible with methods employing xenon or krypton.

BRIEF DESCRIPTION OF THE DRAWINGS

For a more complete understanding of the present invention, reference may be had to the following detailed description considered in conjunction with the accompanying drawings, in which:

FIG. 1 is a partial cross-sectional view of a scintigraphy apparatus constructed in accordance with one exemplary embodiment of the present invention;

FIG. 2 is a side elevational view of an aerosol generation and inhalation unit employed by the scintigraphy apparatus illustrated in FIG. 1, a deflector assembly and an injection port assembly of such unit being shown in crosssection in order to facilitate consideration and discussion;

FIG. 3 is an exploded view of the deflector assembly illustrated in FIG. 2; and

FIG. 4 is a detailed cross-sectional view of the injection port assembly illustrated in FIG. 2.

DESCRIPTION OF THE EXEMPLARY EMBODIMENT

Referring to FIGS. 1 and 2, a scintigraphy apparatus 10 has a housing 12 which comprises an upper lid portion 14 and a lower container portion 16. The housing 12 is lined with a substance 18, such as lead or the like, which is impermeable by radiation. The only outlet from the housing 12, when the lid portion 14 is locked in place on the container portion 16, is a portal 20 at the juncture 22 of the lid portion 14 and container portion 16. The lower container portion 16 has an ultrasonic generator 24 of any suitable design removably mounted at its bottom 26. One example of such a generator 24 has a piezoelectric crystal (not shown) and is powered by an external electrical source preferrably at a frequency from 2.1 MHz to about 2.7 MHz. The electrical power source and the connection of the generator 24 thereto are not shown. The construction of suitable ultrasonic generators and power sources is well known in the art and requires no further elaboration. Above, and in direct contact with, the generator 24 there is placed a container 28 which is filled with a suitable sound-conducting medium 30, for example water.

An aerosol generation and inhalation unit 31 is received in the housing 12 of the scintigraphy apparatus 10. The aerosol generation and inhalation unit 31 includes a nebulizing unit 32 having an upper main chamber 34 and a hemispherically-shaped lower chamber 36 protruding downwardly from the upper main chamber 34 and including a diaphragm 38. A depression 40, which is formed near a lower edge of the upper main chamber 34, extends partway down into the diaphragm 38. The depression 40 allows any gases, which may form at the interface 42 of the sound-conducting medium 30 due to the ultrasonic energy, to escape and migrate upwardly along an outer surface 44 of the upper main chamber 34. The diameter of the diaphragm 38 is chosen such that a radioactively-labelled substance placed therein has an area at its surface which is sufficiently large to allow for good aerosol production even when the volume of the substance is small. A diameter of from 40 mm to about 50 mm has proven highly suitable for this purpose. The hemispherical shape of the diaphragm 38 is intended to allow optimal utilization of space and sound. Experimentation has shown that the size of the particles generated by the ultrasound is correlated to the thickness and density of the diaphragm 38 and it has subsequently been determined that it is extremely important for the diaphragm 38 to have a thickness of between 0.01 mm to about 0.1 mm, and preferrably between 0.02 mm and 0.03 mm. A modified polyethylene has proven to be an extremely suitable material from which to make the diaphragm 38. The modified polyethylene has a density of from 0.950 g/cm$^3$ to about 0.954 g/cm$^3$ at 23° C. as determined according to DIN 53479 and a melting index of from 5.8 g/10 min. to about 7.3 g/10 min. as determined according to DIN 53735. Such a modified polyethylene is available from BASF Kunststoffe Corp. under the name LUPOLEN 5031L.

The nebulizing unit 32 is suspended in the lower container portion 16 above the ultrasonic generator 24 such that the diaphragm 38 protrudes downwardly into the medium container 28. The medium container 28 is filled with a sufficient amount of the medium 30 to substantially immerse the diaphragm 38 in the medium 30.

The upper main chamber 34 has an injection port assembly 46 on its top 48, through which a radio-labelled substance can be injected into the nebulizing chamber 32. A filter 50, suitable for filtering the radioactive aerosol, is contiguous with the nebulizing unit 32 at one side of the upper main chamber 34. Exhaled air passes through the filter 50, which has slits (not shown) in its housing 52 to provide for air exchange. The slits can be arranged in an overlapping fashion to ensure complete shielding and can be provided on a side of the housing 52.

A tubular airway 54 is also connected to the side of the upper main chamber 34 opposite the filter 50 and is likewise contiguous with the nebulizing unit 32. A deflector assembly 56 is positioned in a deflector housing 58 which comprises a portion of the airway 54 and is located adjacent to the upper main chamber 34. The remainder of the length of the airway 54, which extends outwardly from the housing 58, comprises an inhalation tube 60 having a mouthpiece 62 at its terminal end. The nebulizing unit 32 is seated in the lower container portion 16 so that the deflector housing 58 rests in the portal 20 of the housing 12. The portal 20 has a configuration which includes a gasket 64 such that a seal exists between the portal 20 and the deflector housing 58.

Figure 2:
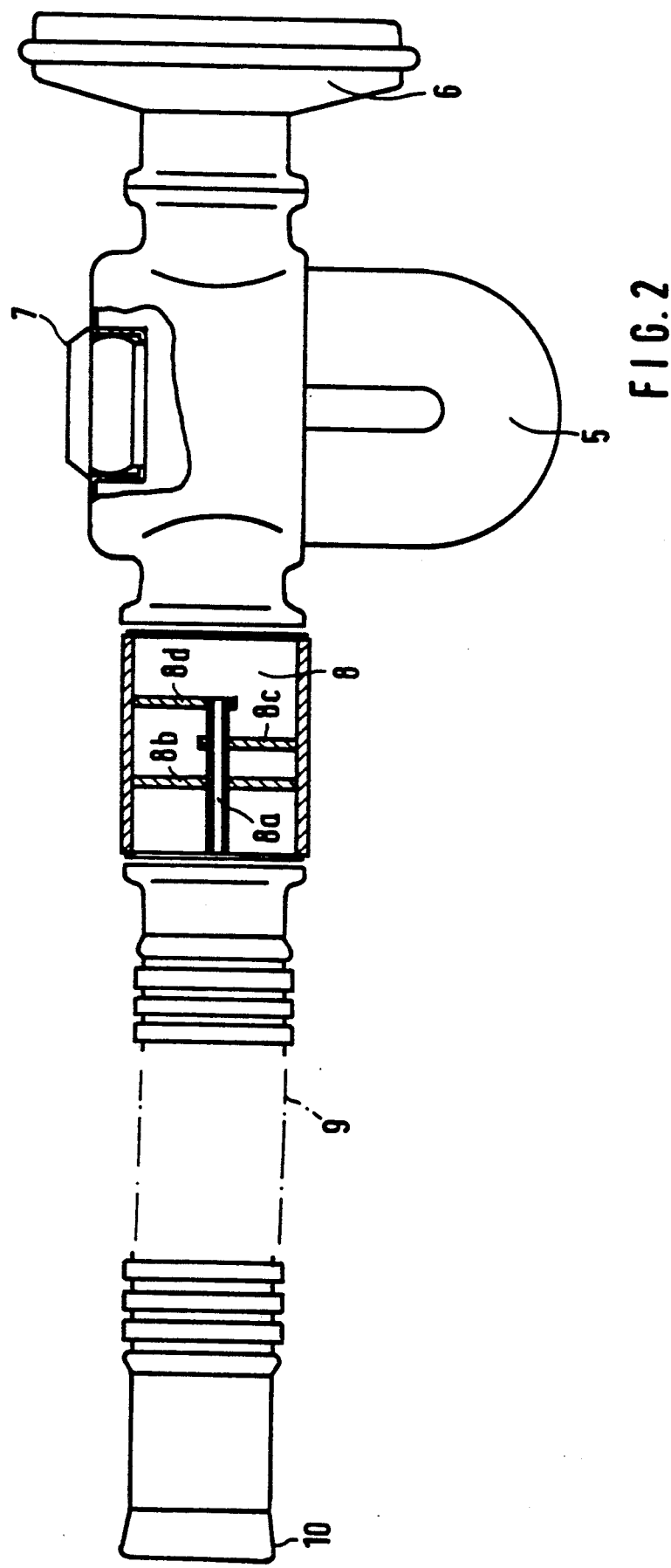
Figure 3:
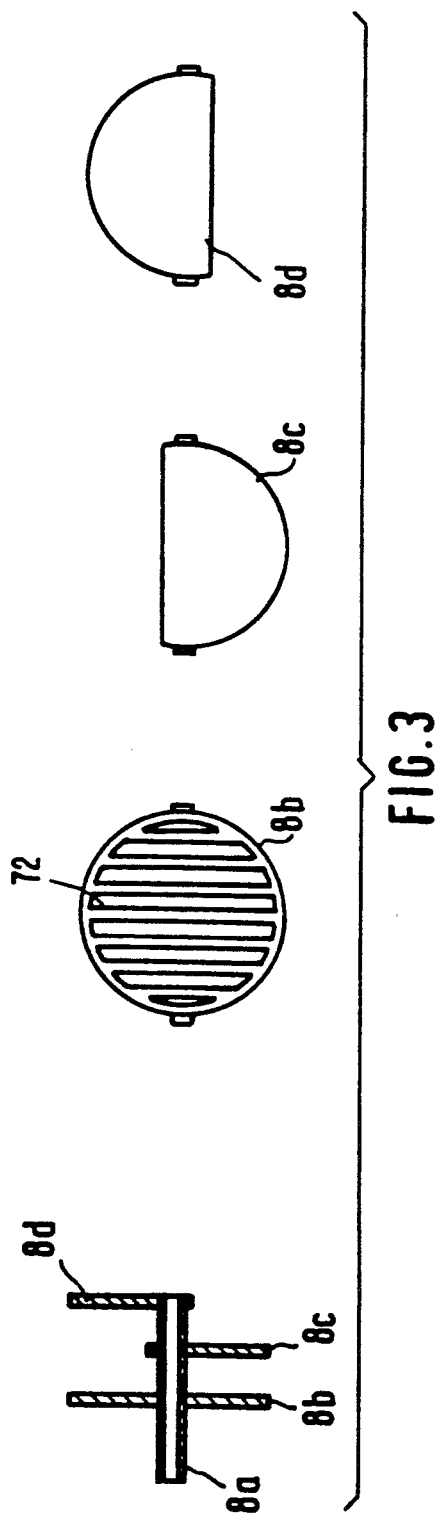

With reference to FIGS. 2 and 3, the deflector assembly 56 includes a plurality of deflectors 62, 64 and 66. In the preferred embodiment of the present invention, there are three deflectors 62, 64 and 66, the deflector 62 having a circular shape and the deflectors 64 and 66 having a semicircular shape. The deflectors 62, 64 and 66 are held in the deflector housing 58 such that they are arranged perpendicular relative to the longitudinal axis of the airway 54. The deflector housing 58 has slots 68, which run parallel to the longitudinal axis of the airway 54 and which are adapted to receive protuberances 70 provided on the peripheries of the deflectors 62, 64 and 66. The deflector 62, which functions to form a fluid-tight seal with the deflector housing 58 when seated therein, has several slits 72, the ends of which are a predetermined minimum distance from the wall of the deflector housing 58 to thereby prevent collected condensate from passing further along into the inhalation tube 60. The deflectors 64 and 66 are mounted diametrically opposite to one another such that the deflector 64 would deflect one-half of an air stream passing through the airway 54 while the deflector 66 would deflect the other half of the air stream.

Figure 4:
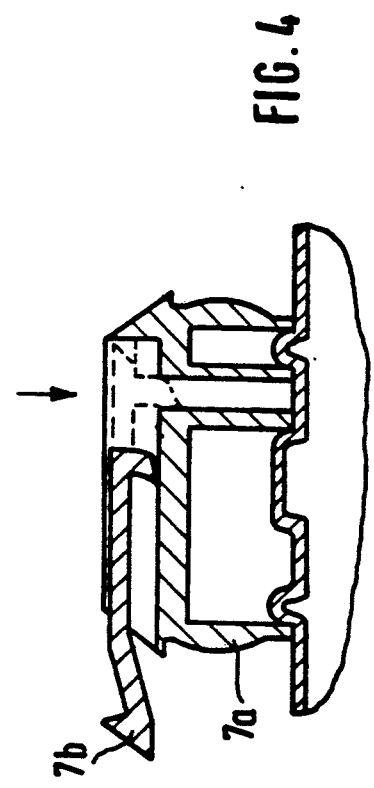

Referring now to FIG. 4, the injection port assembly 46 has an inlet 74 at a lower end 76 of a small tube 78 through which a desired substance is injected into the nebulizing unit 32, preferrably using a syringe. A locking mechanism 79 includes a slide bar 80 having a cross-section which matches a slot 82 in the top of the injection port 46 and which, when the slide bar 80 is pushed into the slot 82, completely covers the upper end 84 of the small tube 78. The slide bar 80 has a downwardly extending barb 86 at the end adjacent to the inlet 74 and an upwardly projecting barb 88 at its other end. The barb 86 has a cross section which corresponds to that of the small tube 78 such that the barb 86 is irreversibly locked into place in the upper end 84, when the barb 86 is slid over the upper end 84 of the small tube 78. The barb 86 is forced down into the upper end 84 of the small tube 78 by pressure transferred from the barb 88 through the slide bar 80. The locking mechanism 79 functions to prevent the aerosol generation and inhalation unit 31 from being reused, thereby avoiding any risk of bacterial or radiation-related contamination.

EXAMPLE

The aerosol generation and inhalation unit 31 is placed into the lower container portion 16 of the housing 12 so that the diaphragm 38 of the nebulizing unit 32 is received into the container 28 and the deflector housing 58 is seated in the portal 20 of the housing 12. Water is poured into the container 28 until the diaphragm 38 is substantially submerged therein.

At least 3 mls. of a radioactively labelled substance is injected by syringe into the nebulizing unit 32 through the sealed inlet 74 of the injection port assembly 46. The radioactively labelled substance is preferrably a colloid having a particle size less than 2 microns and derived from human serum albumin by a process disclosed in U.S. Pat. No. 4,410,507, the specification of which is incorporated herein by reference. The colloid is labelled with $^{99m}$Tc and is diluted to give it a radioactivity amount of from 10 mCi to about 15 mCi in 3 mls. to about 8 mls. of water. The slide bar 80 on the injection port assembly 46 is then pushed in the direction of the arrow 90 until it locks permanently in place over the upper end 84 of the small tube 78.

The upper lid portion 14 of the housing 12 is the secured over the lower container portion 16 of the housing 12 and the patient places the mouthpiece 62 of the airway 54 in her mouth. The ultrasonic generator 24 having a frequency of from 2.1 MHz to about 2.7 MHz is activated and the sound waves are transmitted by the water 30 to the diaphragm 38 which vibrates in response thereto. The vibrations nebulize the labelled substance into a mist of particles, a large proportion of which have a size less than 2 microns. The patient then inhales and exhales through the airway 54 a desired number of times. After the aerosol has been administered to the patient, the housing 12 is opened and the aerosol generation and inhalation unit 31 is removed in one piece and easily disposed of. The patient is then scanned using an appropriate device.

It will be understood that the embodiment described herein is merely exemplary and that a person skilled in the art may make many variations and modifications without departing from the spirit and scope of the invention. All such variations and modifications are intended to be included within the scope of the invention as defined in the appended claims.

I claim:

1. A disposable device for generating and delivering radioactively-labelled pulmonary scintigraphy aerosols, comprising:
   a nebulizing chamber, said nebulizing chamber comprising a wall and said wall having a portion thereof defining a hemispherical membrane, said hemispherical membrane having a thickness of 0.02 mm to 0.03 mm;
   an injection port in a side of said nebulizing chamber opposite said hemispherical membrane, said injection port having an opening and an irreversibly locking cover means for covering said opening without being able to be reversed to uncover said opening;
   an inhalation tube contiguous at one end thereof with an upper portion of said nebulizing chamber and extending laterally therefrom, said inhalation tube including therein condensate deflector means for trapping any condensate of said aerosol and being shaped so as to receive a mouthpiece at an end thereof distal from said nebulizing chamber; and
   air filter means contiguous with an upper portion of said nebulizing chamber opposite said inhalation tube for retaining any solid particles of said aerosol from air exhaled through said inhalation tube and said nebulizing chamber;
   wherein said nebulizing chamber has at least one depression formed in one wall of said nebulizing chamber, said depression extending at least partially into said hemispherical membrane portion thereby allowing gases which may be formed to escape and migrate upwards along said wall of said nebulizing chamber.

2. A device in accordance with claim 1, wherein said hemispherical membrane is made from a modified polymer having a density of from 0.950 g/cm³ to about 0.954 g/cm³ at 23° C. as determined according to DIN 53479 and a melting index of from 5.8 g/10 min. to about 7.3 g/10 min. as determined according to DIN 53735.

3. A device in accordance with claim 2, wherein said locking cover means comprises a sliding bar having a protuberant locking tooth, said locking tooth having a width corresponding in size to said opening, said sliding bar being guided and restricted to horizontal motion by two parallel grooves.

4. A disposable device for generating and delivering radioactively-labelled pulmonary scintigraphy aerosols, comprising:
   a nebulizing chamber, said nebulizing chamber comprising a wall and said wall having a portion thereof defining a hemispherical membrane, said hemispherical membrane having a thickness of 0.02 mm to 0.03 mm;
   an injection port in a side of said nebulizing chamber opposite said hemispherical membrane, said injection port having an opening and an irreversibly locking cover means for covering said opening without being able to be reversed to uncover said opening;
   an inhalation tube contiguous at one end thereof with an upper portion of said nebulizing chamber and extending laterally therefrom, said inhalation tube including therein condensate deflector means for trapping any condensate of said aerosol and being shaped so as to receive a mouthpiece at an end thereof distal from said nebulizing chamber; and
   air filter means contiguous with an upper portion of said nebulizing chamber opposite said inhalation tube for retaining any solid particles of said aerosol from air exhaled through said inhalation tube and said nebulizing chamber;
   wherein said hemispherical membrane has a diameter of from 40 mm to about 50 mm.

5. In a process for scintigraphic imaging of pulmonary ventilation through inhalation of an aerosol of a carrier substance labelled with $^{99m}$Technitium, the improvement comprises:
   using as a carrier substance for $^{99m}$Tc an aqueous colloidal suspension of human serum albumin, the particles of which have an irregular surface structure and a narrow range of particle size, the upper limit thereof being about 2 micrometers; and
   generating an aerosol from said colloidal suspension in a device comprising a nebulizing chamber, said nebulizing chamber having a portion of a wall formed into a hemispherical membrane, said hemispherical membrane having a thickness of 0.02 mm to 0.03 mm, an injection port in a side of said nebulizing chamber opposite said hemispherical membrane having an opening and irreversibly locking cover means for covering said opening, an inhalation tube contiguous at one end with an upper side of said nebulizing chamber and extending laterally therefrom, said inhalation tube including therein condensate deflector means for trapping any condensate of said aerosol and being shaped so as to receive a mouthpiece at an end distal from said nebulizing chamber, and air filter means contiguous with an upper side of said nebulizing chamber opposite said inhalation tube for retaining any solid particles of said aerosol from air exhaled through said inhalation tube and said nebulizing chamber, said step of generating an aerosol comprising placing said nebulizing chamber with its semi-spherical membrane portion in an ultrasound-transmitting fluid, said fluid itself resting upon an ultrasonic vibrator placed in the lower part of an adequately shielded housing, introducing said colloidal suspension in to said nebulizing chamber through said opening of said injection port, irreversibly closing said opening by closing said cover means, placing an upper part of said housing upon said lower part thereof, connecting a removable mouthpiece to the end portion of said inhalation tube, placing said tube in the mouth of a person to be examined, and operating said ultrasonic vibrator to generate ultrasound waves at a frequency of from 2.1 MHz to about 2.7 MHz to generate an aerosol so that natural respiration smoothly draws the ultrasound-generated aerosol into the respiratory tract of the person.

6. The improved process of claim 5, wherein said hemispherical membrane has a diameter of from 40 mm to about 50 mm.

7. The improved process of claim 5, wherein said aqueous colloidal suspension has particles with an upper size limit of 0.2 microns.

8. A device for generating and delivering radioactively-labelled pulmonary scintigraphy aerosols, comprising:
- a radiation impermeable container having an ultrasound generating means therein for generating ultrasound waves at a frequency of 2.1 to 2.7 MHz;
- a nebulizing chamber in said container, said nebulizing chamber comprising a wall and said wall having a portion thereof defining a hemispherical membrane, said hemispherical membrane having a thickness of 0.02 mm to 0.03 mm;
- an injection port in a side of said nebulizing chamber opposite said hemispherical membrane, said injection port having an opening and an irreversibly locking cover means for covering said opening without being able to be reversed to uncover said opening;
- an inhalation tube contiguous at one end thereof with an upper portion of said nebulizing chamber and extending laterally therefrom, said inhalation tube including therein condensate deflector means for trapping any condensate of said aerosol and being shaped so as to receive a mouthpiece at an end thereof distal from said nebulizing chamber; and
- air filter means contiguous with an upper portion of said nebulizing chamber opposite said inhalation tube for retaining any solid particles of said aerosol from air exhaled through said inhalation tube and said nebulizing chamber

* * * * *